United States Patent
Charles et al.

(10) Patent No.: US 11,147,804 B2
(45) Date of Patent: Oct. 19, 2021

(54) ORAL SOLID DOSAGE FORM OF AMLODIPINE AND VETERINARY USES THEREOF

(71) Applicant: CEVA SANTE ANIMALE, Libourne (FR)

(72) Inventors: Romain Charles, Meslay du Maine (FR); Rosita Garcia, Change (FR)

(73) Assignee: CEVA SANTE ANIMALE, Libourne (FR)

( * ) Notice: Subject to any disclaimer, the term of this patent is extended or adjusted under 35 U.S.C. 154(b) by 0 days.

(21) Appl. No.: 15/563,300

(22) PCT Filed: Mar. 31, 2016

(86) PCT No.: PCT/EP2016/057172
§ 371 (c)(1),
(2) Date: Sep. 29, 2017

(87) PCT Pub. No.: WO2016/156550
PCT Pub. Date: Oct. 6, 2016

(65) Prior Publication Data
US 2018/0117023 A1 May 3, 2018

(30) Foreign Application Priority Data
Apr. 1, 2015 (WO) ............... PCT/EP2015/057194

(51) Int. Cl.
| A61K 31/4422 | (2006.01) |
| A61K 9/20 | (2006.01) |
| A61K 45/06 | (2006.01) |
| A61K 9/28 | (2006.01) |

(52) U.S. Cl.
CPC ........ *A61K 31/4422* (2013.01); *A61K 9/2009* (2013.01); *A61K 9/2013* (2013.01); *A61K 9/2018* (2013.01); *A61K 9/2054* (2013.01); *A61K 9/2866* (2013.01); *A61K 45/06* (2013.01)

(58) Field of Classification Search
None
See application file for complete search history.

(56) References Cited

U.S. PATENT DOCUMENTS

| 4,430,333 A | 2/1984 | Campbell et al. | |
| 2001/0036954 A1* | 11/2001 | Foster | A61K 9/0056 514/354 |
| 2003/0069221 A1* | 4/2003 | Kosoglou | A61K 31/337 514/210.02 |
| 2008/0305158 A1 | 12/2008 | Chaudhari et al. | |
| 2009/0117197 A1* | 5/2009 | Bascomb | A61K 31/138 424/523 |
| 2013/0203692 A1* | 8/2013 | Soll | A01N 43/80 514/30 |
| 2014/0302125 A1* | 10/2014 | Kodgule | A61K 31/138 424/451 |

FOREIGN PATENT DOCUMENTS

| WO | WO 2005/032553 | 4/2005 |
| WO | WO 2006/070248 | 7/2006 |
| WO | WO 2008/062435 | 5/2008 |
| WO | WO 2009/110010 | 9/2009 |
| WO | WO 2011/102702 | 8/2011 |
| WO | WO 2011/141381 | 11/2011 |

OTHER PUBLICATIONS

International Search Report and Written Opinion of the ISA for PCT/EP2016/057172, dated May 20, 2016, 11 pages.
Du et al., "Mineralocorticoid receptor blockage and calcium channel blockade have different renoprotective effects on glomerular and interstitial injury in rats", AJP-Renal Physiol, vol. 297, Jun. 17, 2009, pp. F802-F808.
Brown et al., "Guidelines for the Identification, Evaluation, and Management of Systemic Hypertension in Dogs and Cats", J Vet Intern Med, 2007, pp. 542-558.

* cited by examiner

*Primary Examiner* — Kyung S Chang
(74) *Attorney, Agent, or Firm* — Nixon & Vanderhye P.C.

(57) ABSTRACT

The invention relates to the field of animal health. In particular, the invention relates to an oral solid dosage form comprising, as pharmaceutically active compounds, amlodipine. The invention relates to an oral solid dosage forms comprising an amlodipine besylate according to a particular posology for the treatment of hypertension in non-human mammal animals.

3 Claims, No Drawings

ORAL SOLID DOSAGE FORM OF AMLODIPINE AND VETERINARY USES THEREOF

This application is the U.S. national phase of International Application No. PCT/EP2016/057172 filed 31 Mar. 2016, which designated the U.S. and claims priority to International Application No. PCT/EP2015/057194 filed 1 Apr. 2015, the entire contents of each of which are hereby incorporated herein by reference.

The invention relates to the field of animal health. In particular, the invention relates to an oral solid dosage form comprising, as part of the pharmaceutically active compounds, amlodipine. The invention relates to an oral solid dosage forms comprising an amlodipine besylate according to a particular posology for the treatment of hypertension in non-human mammal animals.

BACKGROUND OF THE INVENTION

Amlodipine, 3-ethyl-5-methyl-(+−)-2-[(2-aminoethoxy) methyl]-4-(2-chlorophenyl)-1,4-dihydro-6-methylpyridine-3,5-dicarboxylate, is disclosed in U.S. Pat. No. 4,430,333. Amlodipine is a calcium channel blocker developed for the treatment of human hypertension and other medical indications such as anti ischaemic and angina-alleviating agent.

It exists in various salt forms of amlodipine and especially amlodipine besylate commercially available as Norvasc® (Pfizer) for humans in the form of oral tablets in 2.5 mg, 5 mg and 10 mg base preparations.

Veterinarians use Norvasc® to treat hypertension of non human mammals and especially small animals such as dogs and cats (North America Companion Animal Formulary, sixth edition 2004, published by North America Compendiums Inc). For cats and dogs, the doses are 0.625 to 1.25 mg/cat/day and 0.625 mg/dog/day. This used to mean ⅛ to ¼ of a 5 mg Norvasc® tablet which is a non scored tablet. Consequently, the non observance of the hypertension treatment is usually observed.

Moreover, amlodipine besylate and especially Norvasc® is not readily accepted by most animals due to a strong odor and/or a bad taste (such as a metallic taste). Thus, such tablets have to be force-fed to the animals or mixed with food prior to application.

The problem underlying the present invention was to provide an amlodipine solid formulation readily acceptable by non-human mammal animals, especially small animals.

Also, the aim of the present invention was to provide oral amlodipine besylate solid formulation readily acceptable by non-human mammal animals, especially small animals. The formulation must therefore be well assimilated and have a good palatability to be therapeutically effective. Indeed, the requirements to be met by a solid pharmaceutical formulation suitable for administration to non-human mammal animals are diverse: good palatability by the animals, in the best case voluntary intake, good storage stability, especially low tendency to absorb water, good mechanical properties, especially tablet hardness, good disintegration and release properties.

The present invention is thus directed towards preparation of a palatable oral solid dosage form of amlodipine besylate which is homogenously dispersed. The solid oral formulation of the present invention involves the use of specific pharmaceutically and/or physiologically acceptable carriers with amlodipine besylate.

SUMMARY OF THE INVENTION

This present invention relates to an oral solid dosage form comprising amlodipine besylate, which is homogenously dispersed in croscarmellose sodium, colloidal anhydrous silica and at least one flavoring agent acceptable to non-human mammal animals and especially to small animals.

The present invention also provides a method for preparing an oral solid dosage form according to the invention.

More specifically, the oral solid dosage form is for use in the hypertension treatment of non-human mammals.

DETAILED DESCRIPTION

The present invention relates to an oral solid dosage form comprising amlodipine besylate, croscarmellose sodium, colloidal anhydrous silica, at least one flavoring agent, and optionally further physiologically acceptable carriers.

In a particular embodiment; the oral solid dosage form comprising amlodipine besylate, which is homogenously dispersed in croscarmellose sodium, colloidal anhydrous silica and at least one flavoring agent, and optionally further physiologically acceptable carriers.

According to a particular embodiment, the oral solid dosage form comprises amlodipine besylate in an amount of amlodipine base ranging from 0.5 to 0.75% by weight of the total weight of the solid dosage form. Preferably, said amount of amlodipine base is from 0.6 to 0.7%, more particularly 0.625%.

The strength of the solid dosage form is expressed in terms of amlodipine base, i.e., without the salt.

The term "oral solid dosage form" as used herein includes conventionally used dosage forms for oral administration, such as tablets, granules, capsules and the like. Preferably, the solid dosage form is a tablet.

The invention preferably also relates to an oral solid dosage form according to the invention, characterized in that the weight of the whole solid form is in the range of 50 to 1000 mg, with a more preferred weight range of 100 mg to 600 mg. The solid dosage form is more particularly a tablet, and can be of 100 mg, 200, 300, 400 or 500 mg.

In the context of the invention, the term "homogenously dispersed" more particularly refers to the uniformity of content of amlodipine besylate within the oral solid dosage form.

According to the invention, the term "comprise(s)" or "comprising" (and other comparable terms, e.g., "containing," and "including") is "open-ended" and can be generally interpreted such that all of the specifically mentioned features and any optional, additional and unspecified features are included. According to specific embodiments, it can also be interpreted as the phrase "consisting essentially of" where the specified features and any optional, additional and unspecified features that do not materially affect the basic and novel characteristic(s) of the claimed invention are included or the phrase "consisting of" where only the specified features are included, unless otherwise stated.

Unless defined otherwise, all technical and scientific terms used herein have the same meanings as commonly understood by one of ordinary skill in the art to which this invention belongs. All given ranges and values may vary by 1 to 5% unless indicated otherwise or known otherwise by the person skilled in the art. Accordingly, the term "about" is not used in the description.

According to the invention, the term "flavoring agent(s)" can be generally interpreted such that all ingredients or compound might be added to composition dough to improve palatability or quality to the oral solid dosage form, such as proteins, fats, carbohydrates, yeasts and a mixture thereof. According to a particular embodiment, such flavoring agents according to the invention preferably are selected from artificial or natural beef flavours, artificial or natural chicken flavours, pork liver extract, artificial meat flavour, honey flavor, yeast (such as malted yeast), and a mixture thereof. The flavoring agents are employed in the solid dosage form of the invention in an amount of 10-40% by weight, based on the total weight of the solid dosage form, preferably 20-30% by weight, in particular 20-25% by weight.

According to a particular embodiment, the solid dosage form comprises croscarmellose sodium in an amount of 1-10% by weight, based on the total weight of the solid dosage form, preferably 2-10% by weight, in particular 3, 4, 5 or 6% by weight.

According to a particular embodiment, the solid dosage form comprises colloidal anhydrous silica in an amount of 0.01-5% by weight, based on the total weight of the solid dosage form, preferably 0.02-2% by weight, in particular 0.06, 0.07, 0.08, 0.09, 0.1, 0.11, 0.12 or 0.13% by weight.

As mentioned above, the oral solid dosage form may further comprise physiologically acceptable carriers. The term "physiologically acceptable carriers" as used herein includes one or more of diluents, binders, desiccants, disintegrants, coloring agents, stabilizers, lubricants/glidants, plasticizers and preservatives, suitable for an oral solid dosage forms and non-human mammal animals, such as small animals (e.g. cats and dogs). The excipients are selected based on the desired physical aspects of the final solid dosage forms; e.g., obtaining a tablet with desired hardness and friability, being rapidly dispersible and easily swallowed, etc.

Suitable disintegrants may include, in addition to croscarmellose sodium, one or more of sodium starch glycolate, crospovidone, low substituted hydroxypropyl cellulose, and mixtures thereof.

Suitable binders may include one or more of methyl cellulose, hydroxypropyl cellulose, hydroxypropyl methylcellulose, polyvinylpyrrolidone, gelatin, gum arabic, ethyl cellulose, polyvinyl alcohol, pullulan, pregelatinized starch, agar, tragacanth, sodium alginate, and mixtures thereof.

Suitable diluents may include one or more of cellulose powdered, dextrates, dextrins, dextrose excipients, fructose, kaolin, lactitol, lactose, mannitol, sorbitol, starch, starch pregelatinized, sucrose, sugar compressible, sugar confectioners, and mixtures thereof. According to a particular embodiment, the diluent is mannitol.

According to a particular embodiment, the solid dosage form comprises microcrystalline cellulose, preferably in an amount of 20-50% by weight, based on the total weight of the solid dosage form, preferably 25-40% by weight, in particular 28-35%, and more specifically 29, 30, 31, 32, 33, 34, or 35% by weight.

Suitable lubricants and/or glidants may include, in addition to colloidal anhydrous silica, one or more of magnesium stearate, stearic acid, magnesium stearate, calcium stearate, talc, hydrogenated castor oil, sucrose esters of fatty acid, microcrystalline wax, yellow beeswax, white beeswax, and mixtures thereof. According to a particular embodiment, the solid dosage form comprises magnesium stearate, preferably in an amount of 0.05-5% by weight, based on the total weight of the solid dosage form, preferably 0.8-2% by weight, in particular 0.9, 1.0, 1.1, 1.2, 1.3, 1.4, 1.5, 1.6 or 1.7% by weight.

According to a very specific embodiment, the solid dosage form is a tablet, and more particularly comprises the following ingredients:

| Name of ingredient | Quantity per tablet (mg) |
|---|---|
| (Amlodipine besylate) | (1.73) |
| Amlodipine base | 1.25 |
| Chicken flavor | 5.00 |
| Malted yeast | 38.00 |
| Microcrystalline cellulose | 63.04 |
| Sodium croscarmellose | 10.00 |
| Magnesium stearate | 2.60 |
| Colloidal anhydrous silica | 0.20 |
| Mannitol QS | 200.00 |

According to a particular embodiment, the oral solid dosage form of the invention also comprises at least one Angiotensin Converting Enzyme Inhibitor (ACEI) or an aldosterone antagonist, as a combination product for a simultaneous, separate or sequential use. When used simultaneously, amlodipine besylate and the other active ingredient selected from Angiotensin Converting Enzyme Inhibitors (ACEI) or an aldosterone antagonist may be comprised in the same oral solid form. Angiotensin Converting Enzyme Inhibitors (ACEI) and aldosterone antagonists are as defined below.

The present invention also provides a process for producing the oral solid dosage form, in which the solid dosage form is produced by a process comprising the steps: a) the flavoring agent is mixed with croscarmellose sodium and amlodipine besylate, and optionally with cellulose microcrystalline; b) the mixture of a) is sieved and optionally de-agglomerated; c) colloidal anhydrous silica is added to the mixture of b); and d) optionally a lubricant, such as magnesium stearate, is added to the mixture of c); and e) the mixture of c) or d) is blended for uniformity of granules to obtain final granules; and/or f) optionally the final granules of e) are compressed to form solid formulations, such as tablets.

Step f) is omitted if the solid dosage form is a granule. If the solid dosage form is a capsule, step f) is replaced by step g) that is carried out as to form capsules from granules.

According to a particular embodiment, the process comprises a preceding step of weighing each of the ingredients and/or raw materials.

According to particular embodiment, amlodipine besylate and microcrystalline cellulose are mixed together previously and then added to the mixture of a).

According to an alternative of the process, colloidal anhydrous silica is added at step a) (according to this alternative, step c) is omitted). Consequently, the process for producing the solid dosage form, may comprise the following steps: a) the flavoring agent is mixed with croscarmellose sodium, colloidal anhydrous silica, and amlodipine besylate, and optionally with cellulose microcrystalline; b) the mixture of a) is sieved and optionally de-agglomerated; and d) optionally a lubricant, such as magnesium stearate, is added to the mixture of b); and e) the mixture of b) or d) is blended for uniformity of granules to obtain final granules; and/or f) optionally the final granules of e) are compressed to form solid formulations, such as tablets.

According to an embodiment, the invention relates to a granule formulation as obtained by the process above that can either be administered in the granular form or as tablets after compressing the final granules to tablets. Therefore, the oral solid dosage form according to the invention preferably is a granule (or a plurality of such granules) or a tablet. The administration of the granules can take place by mixing with food or by offering the granules directly to the non-human mammal animal, e.g. in a bowl. The application of the granular form will allow an individual dosing of amlodipine according to the body weight of the animal.

The tablets according to the invention have surprising advantages. The homogeneity of the blend, in process physical tests, analytical tests on different samplings of the tabletting phase and the controls at release are in compliance with all the specifications. The dissolution profile ensures immediate release of amlodipine. By ensuring an immediate release profile of amlodipine, the amount of drug to be administered can be kept as low as possible, thereby improving the safety profile, which is especially important for long-term treatment.

Furthermore, the dosing accuracy of the tablet is excellent. This is due to the fact that in accordance with the manufacturing process according to this invention, an excellent homogeneity of amlodipine content is achieved. Furthermore, the tablets can be broken into two or four halves so that half or the fourth dose per tablet can be administered. The dosing accuracy and compliance of both the animal and the animal owner are assured. This is even more important since the drug is administered for a chronic condition and long-term treatment.

Also, the palatability (i.e. voluntary acceptance of the tablet with or without food) of the tablet is excellent. As mentioned for the tablets in the examples, palatability during the first 4 weeks was 80% with amlodipine and 59% with placebo. The ease of administration increases therefore compliance with the prescribed treatment regime. This is important since the drug is administered for a chronic condition and long-term treatment.

The invention preferably also relates to an oral solid form characterized in that the oral solid form is stable for at least 24 months at 25° C. and 60% relative humidity.

Testing parameter assays for degradation of amlodipine, dissolution, loss on drying, hardness and disintegration of the tablet were obtained. The tablets according to the invention are within the specification limits regarding degradation of amlodipine, dissolution, loss on drying, hardness and disintegration.

Suitable packaging materials for tablets according to the invention are selected from, but not limited to: aluminum/aluminum blisters, PVC/PVDC blisters, and HDPE (high density polyethylene bottles).

Hypertension is the medical term for high blood pressure, which is a common problem in mammals, and also now recognized as a common condition in non human mammals, such as small animals (i.e. dogs and cats).

Feline hypertension is commonly found as a complication of other underlying medical conditions (so-called 'secondary or systemic hypertension'), although primary hypertension (hypertension without any underlying disease) may also be seen in cats. In contrast to human, where primary hypertension (also called "essential hypertension") is most common, systemic hypertension is more common in cats. Systemic hypertension in cats is most commonly associated with acute or chronic kidney disease (CKD). Other conditions associated with the development of secondary hypertension in cats include hyperthyroidism, diabetes mellitus (DM), primary hyperaldosteronism, and pheochromocytoma. Chronically sustained increases in Blood Pressure (BP) cause injury to various tissues, mainly to kidneys, eyes, brain, and heart. This is commonly referred to as target organ damage (TOD).

According to the guidelines of the American College of Veterinary Internal Medicine (ACVIM) Hypertension Consensus Panel, hypertension is categorized according to its risk of TOD: minimal risk (<150/95 mmHg), mild risk (150-159/95-99 mmHg), moderate risk (160-179/100-119 mmHg), and severe risk (>180/120 mmHg).

The goal of antihypertensive treatment is to maximally decrease the risk of TOD, which is achieved with persistent BP reduction to values<150/95 mmHg.

Thus, the oral solid dosage form according to the invention is more particularly for use in the prevention and/or treatment of non-human mammal animals, more specifically small animals, with hypertension. Said use or treatment may also be in association with an Angiotensin Converting Enzyme Inhibitor (ACEI) or an aldosterone antagonist.

Alone ACE inhibitors are unlikely to control hypertension. They may provide additional blood pressure control with amlodipine and should preferably be used concurrently, especially if the cat has proteinuria. The Angiotensin Converting Enzyme inhibitors (ACEI) can be for example captopril, enalapril, benazepril, lisinopril, or ramipril.

Treatment with aldosterone antagonist, such as eplerenone, combined with amlodipine provides additive renoprotective effects characterized by reductions in both glomerulosclerosis and tubulointerstitial fibrosis (Du et al., AJP-Renal Physiol, 2009, Vol 297, p 802-808). Aldosterone antagonists are for example epleronone or spironolactone, Systemic hypertension in small animals, such as cats, can be associated with acute or chronic kidney disease. Other conditions associated with the development of secondary hypertension in small animals, such as cats and/or dogs, include hyperthyroidism, diabetes mellitus, primary hyperaldosteronism, and pheochromocytoma. Chronically sustained increases in BP cause injury to various tissues, mainly to kidneys, eyes, brain, and heart.

The oral solid dosage form according to the invention is more particularly for use in the prevention and/or treatment of non-human mammals, more specifically small animals, with systemic hypertension in small animals, such as cats, optionally associated with acute or chronic kidney disease.

The oral solid dosage form according to the invention is more particularly for use in the prevention and/or treatment of non-human mammals, more specifically small animals, with systemic hypertension in small animals, such as cats and/or dogs, optionally associated with hyperthyroidism, diabetes mellitus, primary hyperaldosteronism, and pheochromocytoma. The solid dosage form according to the invention is more particularly for use in the prevention and/or treatment of non-human mammals, more specifically small animals, with hypertension in small animals, such as cats and/or dogs, and/or in the prevention and/or treatment of tissues (such as kidneys, eyes, brain, and/or heart) injuries due to an hypertension in small animals, such as cats and/or dogs.

"Non-human mammal animals" is intended to mean all mammal animals with the exception of human. The non-human animals include domestic, farm, and zoo animals, including cats, dogs, rabbits, cattle, pigs, boars, etc. According to the present description, when cats or dogs are cited by way of example, it can be generalized to any other small animals, such as mice, rats, guinea pigs, golden hamsters, and rabbits. More specifically, it refers to cats and dogs, and preferably to cats.

Furthermore, the invention relates to a method of prevention and/or treatment of diseases wherein hypotensive substances have a therapeutic benefit, comprising administering orally to a non-human mammal animal in need of such treatment a therapeutically effective amount of a solid dosage form as described above.

Preferred is a method of prevention and/or treatment of hypertension, comprising administering orally to a non-human mammal animal in need of such treatment a therapeutically effective amount of an oral solid dosage form according to the invention as disclosed above. Most preferably, the method comprises administering a tablet according to the invention, as defined above.

Furthermore, the invention relates to an oral solid dosage form according to the invention for use in the prevention and/or treatment of a non-human mammal animal with hypertension, where the daily dose of amlodipine is from 0.125-0.25 mg/kg, preferably in a single take.

After 14 or more days of treatment, the dose may subsequently be doubled or increased up to 0.5 mg/kg once daily, for instance, if adequate clinical response has not been achieved (e.g. systolic blood pressure remaining over 150 mmHg or a decrease of less than 15% from the pre-treatment measurement).

The present invention also relates to kits for veterinary usage intended for the treatment of non-human mammal animal affected by hypertension, having at least one compartment, for a separated packaging or not, of solid dosage forms as described above, and optionally having another compartment of another therapy, such as ACEI or aldosterone antagonist. The kits according to the invention may further present a booklet giving instructions for implementing the treatment.

The present invention will be better understood in view of the Examples below.

EXAMPLES

Example 1

Manufacturing Formula for Tablets

| Name of ingredient | Quantity per tablet (mg) |
| --- | --- |
| Amlodipine besylate | 1.73 |
| Amlodipine base | 1.25 |
| Chicken flavor | 5.00 |
| Malted yeast | 38.00 |
| Microcrystalline cellulose | 63.04 |
| Sodium croscarmellose | 10.00 |
| Magnesium stearate | 2.60 |
| Colloidal anhydrous silica | 0.20 |
| Mannitol QS | 200.00 |

Process
1—Amlodipine besylate and Microcrystalline Cellulose PH 102 are mixed manually (5 minutes).
2—Chicken Flavour, Malted Yeast, Amlodipine/Microcrystalline Cellulose-mix, Sodium Crosscarmellose, Mannitol 100 SD, Silica Colloidal Anhydrous and Microcrystalline Cellulose PH 102 (rest) are sieved (1.8 mm) and loaded in the Blender for mixing (25 minutes, 17 rpm).
3—Magnesium Stearate is sieved (1.8 mm) and loaded in blender for mixing (5 minutes, 17 rpm).
Transfer of the mass from the mixer into the container before tabletting
4—Bulk blend is tableted in rotary press:
Oblong tablet, shape tablets, scored, weight tablet: 200 mg
5—Tablets can be packaged in Aluminium/Aluminium Blisters in blistering area.

The obtained tablet is stable for at least 24 months at 25° C. and 60% relative humidity. Testing parameter assays for degradation of amlodipine, dissolution, loss on drying, hardness and disintegration of the tablet were obtained and within the specification limits regarding degradation of amlodipine, dissolution, loss on drying, hardness and disintegration.

Example 2

Uniformity of content was checked on entire tablet from 10 tablets (and three batches) as prepared in example 1. The 10 units (entire) were assayed individually. The methods are as defined by the European Pharmacopeia 5.2 for uniformity of dosage units; the Acceptance value is calculated, as defined in table 2.9.40.-2 of the European Pharmacopeia 5.2.

TABLE 1

| Amlodipine base content | Batch 1 | Batch 2 | Batch 3 |
| --- | --- | --- | --- |
| Mean content (mg/tb) | 1.201 | 1.246 | 1.258 |
| X (%) | 96.11 | 99.74 | 100.67 |
| Standard deviation On the percentages (s) | 2.8012 | 1.5802 | 1.9241 |
| Acceptance value (AV) | 9.11 | 3.8 | 4.6 |
| Results | In compliance | In compliance | In compliance |

X (%) is the mean of individual contents expressed as a percentage of the label claim.

Each individual content in the three batches complies therefore with the requirements of the current EP test Uniformity of dosage units. The Acceptance value is less than L1 for each batch.

Example 3

Uniformity of content was checked on halves, from 10 tablets (and three batches) as prepared in example 1. The 10 units (halves) were assayed individually. The methods are as defined by the European Pharmacopeia 5.2 for uniformity of dosage units; the Acceptance value is calculated, as defined in table 2.9.40.-2 of the European Pharmacopeia 5.2.

TABLE 2

| Amlodipine base content | Batch 1 | Batch 2 | Batch 3 |
| --- | --- | --- | --- |
| Mean content (mg/tb) | 0.598 | 0.624 | 0.625 |
| X (%) | 95.78 | 99.78 | 100.05 |
| Standard deviation On the percentages (s) | 2.9175 | 2.5702 | 2.2145 |
| Acceptance value (AV) | 9.7 | 6.2 | 5.3 |
| Results | In compliance | In compliance | In compliance |

X (%) is the mean of individual contents expressed as a percentage of the label claim.

Each individual content in the three batches complies therefore with the requirements of the current EP test Uniformity of dosage units. The Acceptance value is less than L1 for each batch.

Example 4

Efficacy and Clinical Safety of the Oral Dosage Forms as Prepared in Example 1

Seventy-seven client-owned cats were included in the study (mean age 14 years). The study was randomized, double-blind, placebo controlled, and consisted of two phases. Most cats received an initial single dose of 0.625 mg amlodipine daily. The amlodipine product used in this study was the tablet designed for cats, as described in Example 1. Placebo tablets were equal in size and shape, contained the same excipients but no active ingredient.

In the blinded phase, 42 cats received 0.125 mg/kg (range 0.125-0.25 mg/kg) amlodipine given PO once daily for 14 days. If they responded the dose remained the same to day 28. For non-responders, the dose was increased to 0.25 mg/kg. Thirty-five cats received placebo following the same protocol. Arterial blood pressure was measured using a high definition oscillometry method. At day 28 a responder was defined as a cat showing a decrease of SBP to ≤150 mmHg or a decrease from baseline of at least 15%. After 28 days all cats continued with amlodipine for 2-3 months in an open phase with the placebo cats repeating the same dose escalation protocol as in the blinded phase. Blood pressure was measured in accordance with the ACVIM guidelines (Brown S, Atkins C, Bagley R, et al. Guidelines for the identification, evaluation, and management of systemic hypertension in dogs and cats. J Vet Intern Med 2007; 21:542-558.) using a high definition oscillometry (HDO) device.

The responder rate was 63% in the amlodipine group and 18% in the placebo group following the dose escalation from day 14 being applied to 54% and 80% of cats receiving amlodipine and placebo respectively. Cats receiving amlodipine were 7.9 (95% CI 2.6 to 24.1) times more likely to be classified as responders when compared to those receiving placebo (logistic regression model, p=0.0003). Responders are those which met criteria of responding to treatment (SBP<150 mmHg or a reduction in SBP of 15%). From a baseline value of 181.6±12.5 and 179.3±10.8 mmHg the mean SBP decreased to 153.6±16.9 mmHg with amlodipine and to 167.7±20.5 mmHg with placebo (repeated measures analysis of covariance model, p<0.001) by day 28. The responder rate was not influenced by factors other than amlodipine treatment (e.g. baseline blood pressure, concomitant ACE inhibitor therapy, renal disease).

There were no differences between the amlodipine and placebo groups in the frequency of adverse events reported during the 28-day blinded phase.

Example 5

Palatability Evaluation During the Study as Described in Example 4

Palatability was scored on a 3-point scale during the study: tablet taken spontaneously from hand or from empty bowl (1); tablet taken with food from bowl or administered within palatable food (2); tablet administered directly into mouth (3). Scores 1 and 2 were considered as palatable, while score 3 was considered not palatable. The investigator evaluated palatability and possible changes based on owner's interview and diary data.

Palatability (i.e. voluntary acceptance of the tablet with or without food) during the first 4 weeks was 80% with amlodipine and 59% with placebo. Palatability was stable throughout the study in cats that started with amlodipine but increased somewhat in placebo cats when they started amlodipine treatment. Overall palatability with amlodipine during the 3-month treatment period was 73%. There were no statistical differences between the groups.

The invention claimed is:

1. A veterinary oral solid dosage form, which is a tablet, wherein the tablet comprises the following ingredients:

| Name of ingredient | Quantity per tablet (mg) |
|---|---|
| Amlodipine besylate | 1.73 |
| Chicken flavor | 5.00 |
| Malted yeast | 38.00 |
| Microcrystalline cellulose | 63.04 |
| Sodium croscarmellose | 10.00 |
| Magnesium stearate | 2.60 |
| Colloidal anhydrous silica | 0.20 |
| Mannitol QS | 200.00. |

2. The veterinary oral solid dosage form according to claim 1, which is stable for at least 24 months at 25° C. and 60% relative humidity.

3. The veterinary oral solid dosage form according to claim 1, wherein amlodipine besylate is homogenously dispersed in the tablet.

* * * * *

UNITED STATES PATENT AND TRADEMARK OFFICE
CERTIFICATE OF CORRECTION

PATENT NO. : 11,147,804 B2
APPLICATION NO. : 15/563300
DATED : October 19, 2021
INVENTOR(S) : Charles et al.

It is certified that error appears in the above-identified patent and that said Letters Patent is hereby corrected as shown below:

In the Claims

Claim 3, Column 10, Line 38, change "amlodipine" to --the amlodipine--

Signed and Sealed this
Sixteenth Day of August, 2022

Katherine Kelly Vidal
*Director of the United States Patent and Trademark Office*